US008679736B2

(12) United States Patent
Goodrich et al.

(10) Patent No.: US 8,679,736 B2
(45) Date of Patent: Mar. 25, 2014

(54) REMOVAL OF ADENINE DURING A PATHOGEN REDUCTION PROCESS IN WHOLE BLOOD OR RED BLOOD CELLS BY DILUTION

(75) Inventors: Raymond P. Goodrich, Lakewood, CO (US); Suzann K. Doane, Littleton, CO (US)

(73) Assignee: Terumo BCT Biotechnologies, LLC, Lakewood, CO (US)

( * ) Notice: Subject to any disclaimer, the term of this patent is extended or adjusted under 35 U.S.C. 154(b) by 1132 days.

(21) Appl. No.: 12/640,878

(22) Filed: Dec. 17, 2009

(65) Prior Publication Data

US 2010/0089840 A1 Apr. 15, 2010

Related U.S. Application Data

(60) Continuation of application No. 11/624,487, filed on Jan. 18, 2007, now abandoned, which is a division of application No. 10/423,200, filed on Apr. 24, 2003, now Pat. No. 7,183,045.

(60) Provisional application No. 60/375,849, filed on Apr. 24, 2002.

(51) Int. Cl.
 *A01N 1/02* (2006.01)
 *C12N 13/00* (2006.01)
 *C12N 7/06* (2006.01)

(52) U.S. Cl.
 USPC ........... 435/2; 435/6.1; 435/173.1; 435/173.3

(58) Field of Classification Search
 None
 See application file for complete search history.

(56) References Cited

U.S. PATENT DOCUMENTS

| 3,629,071 A | 12/1971 | Sekhar |
| 3,874,384 A | 4/1975 | Diendoerfer et al. |
| 4,061,537 A | 12/1977 | Seiler et al. |
| 4,112,070 A | 9/1978 | Harmening |
| 4,267,269 A | 5/1981 | Grode et al. |
| 4,321,919 A | 3/1982 | Edelson |
| 4,390,619 A | 6/1983 | Harmening-Pittiglio |
| 4,432,750 A | 2/1984 | Estep |
| 4,572,899 A | 2/1986 | Walker et al. |
| 4,585,735 A | 4/1986 | Meryman et al. |

(Continued)

FOREIGN PATENT DOCUMENTS

| EP | 0196515 | 10/1986 |
| EP | 0754461 | 1/1997 |

(Continued)

OTHER PUBLICATIONS

Yoshihiro Suzuki, Toshiaki Miura and Taketo Ogiso, Riboflavin Photosensitized Hemolysis of Rat Erythrocytes in the Presence of Serum, 1982, J.Pharm.Dyn., vol. 5, pp. 568-575.*

(Continued)

*Primary Examiner* — Blaine Lankford, Jr.
*Assistant Examiner* — Trent R Clarke
(74) *Attorney, Agent, or Firm* — René A. Pereyra; Elizabeth J. Regan; John R. Merkling

(57) ABSTRACT

The methods of this invention involve preventing the formation of a complex between adenine and riboflavin by reducing the amount of adenine in a solution containing blood or blood components to be pathogen reduced.

4 Claims, 4 Drawing Sheets

(56) References Cited

U.S. PATENT DOCUMENTS

| | | |
|---|---|---|
| 4,609,372 A | 9/1986 | Carmen et al. |
| 4,626,431 A | 12/1986 | Batchelor et al. |
| 4,675,185 A | 6/1987 | Kandler et al. |
| 4,695,460 A | 9/1987 | Holme |
| 4,704,352 A | 11/1987 | Miripol et al. |
| 4,769,318 A | 9/1988 | Hamasaki et al. |
| RE32,874 E | 2/1989 | Rock et al. |
| 4,828,976 A | 5/1989 | Murphy |
| 4,925,665 A | 5/1990 | Murphy |
| 4,961,928 A | 10/1990 | Holme et al. |
| 4,992,363 A | 2/1991 | Murphy |
| 4,999,375 A | 3/1991 | Bachynsky et al. |
| 5,234,808 A | 8/1993 | Murphy |
| 5,250,303 A | 10/1993 | Meryman et al. |
| 5,344,752 A | 9/1994 | Murphy |
| 5,360,734 A | 11/1994 | Chapman et al. |
| 5,376,524 A | 12/1994 | Murphy et al. |
| 5,378,601 A | 1/1995 | Gepner-Puszkin |
| 5,459,030 A | 10/1995 | Lin et al. |
| 5,466,573 A | 11/1995 | Murphy et al. |
| 5,474,891 A | 12/1995 | Murphy |
| 5,487,971 A | 1/1996 | Holme et al. |
| 5,569,579 A | 10/1996 | Murphy |
| 5,597,722 A | 1/1997 | Chapman et al. |
| 5,622,867 A | 4/1997 | Livesey et al. |
| 5,709,991 A | 1/1998 | Lin et al. |
| 5,712,085 A | 1/1998 | Wollowitz et al. |
| 5,753,428 A | 5/1998 | Yuasa et al. |
| 5,769,839 A | 6/1998 | Carmen et al. |
| 5,827,640 A | 10/1998 | Wiggins et al. |
| 5,906,915 A | 5/1999 | Payrat et al. |
| 5,908,742 A | 6/1999 | Lin et al. |
| 5,955,256 A | 9/1999 | Sowemino-Coker et al. |
| 5,955,257 A | 9/1999 | Burger et al. |
| 5,962,213 A | 10/1999 | Wiggins et al. |
| 5,965,349 A | 10/1999 | Lin et al. |
| 6,017,691 A | 1/2000 | Wollowitz et al. |
| 6,063,624 A | 5/2000 | Kandler et al. |
| 6,114,107 A | 9/2000 | Wiggins et al. |
| 6,251,580 B1 | 6/2001 | Lin et al. |
| 6,258,577 B1 | 7/2001 | Goodrich, Jr. et al. |
| 6,268,120 B1 | 7/2001 | Platz et al. |
| 6,277,337 B1 | 8/2001 | Goodrich, Jr. et al. |
| 6,277,557 B1 | 8/2001 | Burger et al. |
| 6,326,197 B1 | 12/2001 | Kandler et al. |
| 6,548,241 B1 | 4/2003 | McBurney et al. |
| 6,566,046 B2 | 5/2003 | Lin et al. |
| 6,936,413 B1 | 8/2005 | Bischof et al. |
| 7,183,045 B2 | 2/2007 | Goodrich et al. |

FOREIGN PATENT DOCUMENTS

| | | |
|---|---|---|
| WO | WO85/02116 | 5/1985 |
| WO | WO92/08348 | 5/1992 |
| WO | WO92/08349 | 5/1992 |
| WO | WO94/16099 | 7/1994 |
| WO | WO96/14741 | 5/1996 |
| WO | WO98/41087 | 9/1998 |
| WO | WO98/56247 | 12/1998 |
| WO | WO00/04930 | 2/2000 |
| WO | WO00/11946 | 3/2000 |
| WO | WO01/45502 | 6/2001 |
| WO | WO01/78792 | 10/2001 |
| WO | WO01/94349 | 12/2001 |
| WO | WO01/96340 | 12/2001 |

OTHER PUBLICATIONS

International Search Report for PCT/US03/12969.

Balduini et al, "Cryopreservation of Human Platelets Using Dimethyl Sulfoxide and Glycerol-glucose: Effects on 'in vitro' Platelet Function", *Haematologica* 1983, 78:2:101-4, abstract.

Frati et al, "Degradation of Hyaluronic Acid by Photosensitized Riboflavin in Vitro: Modulation of the Effect by transition Metals, radical Quenchers, and Metal Chelators", *Free Radical Biology & Medicine*, 1997, 22:7:1139-1144, abstract.

Goodrich, R.P. and Platz, M.S., "The design and development of selective, photoactivated drugs for sterilization of blood products," 1997, *Drugs of the Future* 22(2):159-171.

Uehara et al, "Effect of adenine on the riboflavin-sensitized photoreaction. II. Effect of adenine on the photodynamic inactivation of transforming deoxyribonucleic acid in the presence of riboflavin", 1972, *J Biochemistry*, 71:5, 805-810.

Uehara et al, "Effect of adenine on the riboflavin-sensitized photoreaction. I. Effect of adenine on the photodynamic inactivation of yeast alcohol dehydrogenase in the presence of riboflavin," *J. Vitaminology*, 17:3,1971,148-154.

Yu et al, "Hypericin-Induced Phototoxicity in Cultured Fibroblasts and Swine Erythocytes", *Photochemistry and Photobiology*, 1996, 64:1:168-173.

\* cited by examiner

REMOVAL OF ADENINE DURING A PATHOGEN REDUCTION PROCESS IN WHOLE BLOOD OR RED BLOOD CELLS BY DILUTION

PRIORITY CLAIM

This application is a continuation of U.S. application Ser. No. 11/624,487, filed on Jan. 18, 2007, which is a divisional of U.S. non-provisional application Ser. No. 10/423,200, filed Apr. 24, 2003 and now U.S. Pat. No. 7,183,045, which claims priority from U.S. Provisional 60/375,849, filed Apr. 24, 2002.

BACKGROUND OF THE INVENTION

Contamination of blood supplies with infectious microorganisms such as HIV, hepatitis and other viruses and bacteria presents a serious health hazard for those who must receive transfusions of whole blood or administration of various blood components such as platelets, red cells, blood plasma, Factor VIII, plasminogen, fibronectin, anti-thrombin III, cryoprecipitate, human plasma protein fraction, albumin, immune serum globulin, prothrombin, plasma growth hormones, and other components isolated from blood. Blood screening procedures which are currently available may miss contaminants. Thus, there is a need for sterilization procedures that effectively neutralize all infectious viruses and other microorganisms but do not damage cellular blood components, do not degrade desired biological activities of proteins, and preferably do not need to be removed prior to administration of the blood product to the patient.

The use of photosensitizers, compounds which absorb light of a defined wavelength and transfer the absorbed energy to an energy acceptor, has been proposed as a solution to the contamination of blood and blood components. Various photosensitizers have been proposed for use as blood additives for pathogen inactivation of blood or blood components. A review of commonly used photosensitizers, and some of the issues of importance in choosing photosensitizers for decontamination of blood products is provided in Goodrich, R. P., et al. (1997), "The Design and Development of Selective, Photoactivated Drugs for Sterilization of Blood Products," Drugs of the Future 22:159-171.

Some photosensitizers that have been proposed for use for blood component photoirradiation have undesirable properties. For example, European Patent Application 196,515 published Oct. 8, 1986, suggests the use of non-endogenous photosensitizers such as porphyrins, psoralens, acridine, toluidines, flavine (acriflavine hydrochloride), phenothiazine derivatives, and dyes such as neutral red and methylene blue, as blood additives. Another molecule, chlorpromazine, has been used as a photosensitizer; however its usefulness is limited by the fact that it should be removed from any fluid administered to a patient after the decontamination procedure because it has a sedative effect. Protoporphyrin, which occurs naturally within the body, can be metabolized to form a photosensitizer; however, its usefulness is limited in that it degrades the desired biological activities of proteins.

Most preferred with respect to the reduction of pathogens in blood or blood products are endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo. Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavine adenine dinucleotide [FAD]), alloxazine mononucleotide (also known as flavine mononucleotide [FMN] and riboflavine-5-phosphate), vitamin Ks, vitamin L, their metabolites and precursors, and napththoquinones, naphthalenes, naphthols and their derivatives having planar molecular conformations. The term "alloxazine" includes isoalloxazines.

The use of the endogenous alloxazine photosensitizers such as those mentioned above to reduce pathogens which may be contained in blood or blood products are disclosed in U.S. Pat. Nos. 6,258,577 and 6,277,337 issued to Goodrich et. al and are herein incorporated by reference in their entirety to the amount not inconsistent.

Endogenously-based derivative photosensitizers useful in this invention include synthetically derived analogs and homologs of endogenous photosensitizers which may have or lack lower (1-5) alkyl or halogen substituents of the photosensitizers from which they are derived, and which preserve the function and substantial non-toxicity thereof. U.S. Pat. No. 6,268,120 to Platz et al. discloses alloxazine derivatives which may also be used to inactivate microorganisms contained in blood or blood components. This patent is also incorporated by reference into the present invention to the amount not inconsistent.

When certain endogenous photosynthesizers are used, certain components which are naturally occurring in blood plasma or in some synthetic blood storage/collection solutions may interact with the photosensitizer during the photoinactivation process and form complexes. The presence of these complexes may increase the rate of side reactions which occur during the photolysis of the photosensitizer. One such complex which may form if 7,8-dimethyl-10-ribityl isoalloxazine (riboflavin) is used as the photosensitizer, is a complex between riboflavin and adenine. Adenine is found in blood plasma as well as being an additive component of some synthetic blood collection/storage solutions.

It is toward this end of preventing damage to blood and blood components to be pathogen reduced by preventing the formation of a photosensitizer-plasma constituent complex (such as adenine) that the present invention is directed.

Several U.S. Patents discuss the removal of plasma and plasma proteins in a pathogen inactivation process using photosensitizers. U.S. Pat. No. 5,360,734 issued Nov. 1, 1994 and U.S. Pat. No. 5,597,722 issued Jan. 28, 1997 both to Chapman et al. discuss treating a blood component containing red blood cells and plasma proteins by removing a portion of the plasma proteins before adding the photoactive agent benzoporphyrin. The treated blood component is prevented from contacting plasma proteins for a period of time (three to eighteen hours) after treatment to prevent binding of the treated cells to IgG proteins in the plasma. These patents do not disclose or suggest the removal of plasma to prevent the formation of specific plasma constituent-photo sensitizer complexes which changes the efficiency of the photosensitizer.

BRIEF SUMMARY OF THE INVENTION

Adenine is found naturally occurring in small concentrations in plasma and in some synthetic blood collection/storage solutions. One method of this invention involves preventing the formation of a complex between adenine and riboflavin by reducing the amount of adenine in a solution containing blood or blood components to be pathogen reduced by reducing the level of plasma.

Another aspect of this invention involves the collection of blood or blood components to be pathogen reduced into pathogen reduction/storage solutions which are adenine free.

If it is desired to pathogen reduce previously collected blood or blood components which were initially collected and stored in a collection/storage solution containing adenine, another aspect of this invention involves washing the previously collected blood components with saline or like solution, before the pathogen reduction process.

Another method which may be used for reducing the concentration of selected components of plasma such as adenine in a fluid to be pathogen reduced may be by selective filtration.

After removal of adenine by any means known in the art, the fluid containing the blood component to be pathogen reduced is combined with a photosensitizer such as riboflavin and exposed to photoradiation of the appropriate wavelength to activate the photosensitizer. The amount of photoradiation used is sufficient to activate the photosensitizer as described herein, but less than that which would cause non-specific damage to the biological components or substantially interfere with biological activity of other proteins present in the fluid. Non-specific damage is damage that damages all components.

DETAILED DESCRIPTION OF THE INVENTION

The pathogen reduction method of this invention using endogenous photosensitizers and endogenously-based derivative photosensitizers is exemplified herein using 7,8-dimethyl-10-ribityl isoalloxazine as the photosensitizer.

7,8-dimethyl-10-ribityl isoalloxazine (riboflavin or vitamin B2) absorbs light from about 200 to 500 nm. The ring system core of 7,8-dimethyl-10-ribityl isoalloxazine is resistant to photodegradation but the ribityl side chain of riboflavin undergoes photodegradation.

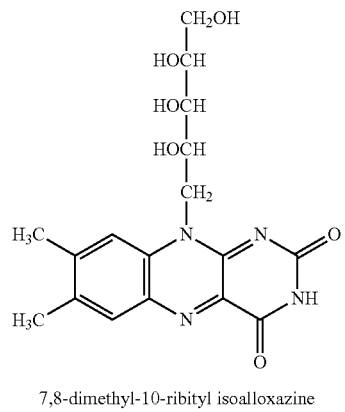

7,8-dimethyl-10-ribityl isoalloxazine 7,8-dimethyl-1D-ribityl isoalloxazine

Photosensitizers of this invention include compounds which preferentially adsorb to nucleic acids, thus focusing their photodynamic effect upon the nucleic acids of microorganisms and viruses with little or no effect upon accompanying cells or proteins. Pathogen kill using riboflavin and related compounds also occurs upon photoinactivation via singlet oxygen damage, thereby disrupting the ability of the pathogen to function and reproduce, or both.

Figure 1:
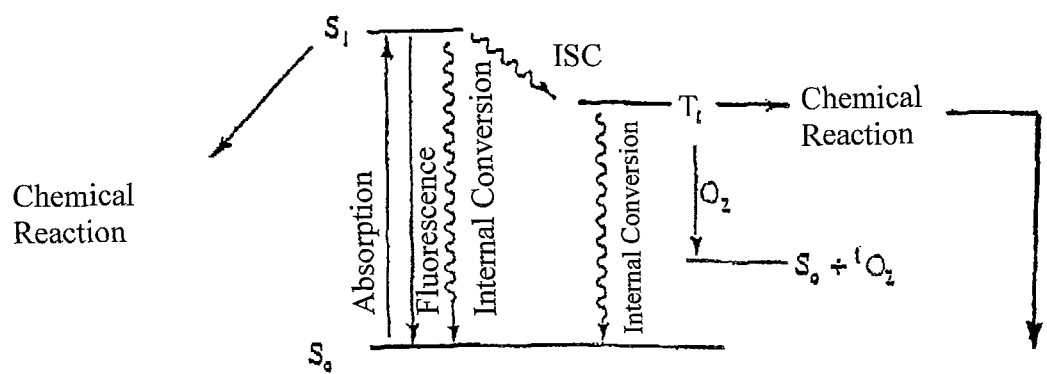
FIG. 1 is a Jablonski diagram showing chemical reactions of 7,8-dimethyl-10-ribityl isoalloxazine (riboflavin and other related compounds) catalyzed by photoradiation, oxygen and other components.

FIG. 1 is a Jablonski diagram showing the photochemical reactions of 7,8-dimethyl-10-ribityl isoalloxazine (riboflavin and other related compounds) which occur upon catalysis by photoradiation, oxygen and other components. The photo sensitizer in its ground state is referred to as $S_0$. Upon absorption of light, riboflavin is converted to an electrically excited state which in condensed phase immediately ($<<10^{-11}$s) relaxes to the lowest vibrational level of the lowest excited state ($S_1$). The lifetimes of $S_1$ states in solution are usually in the range of 1-10 ns and are controlled by internal conversion (IC) and fluorescence (F) decay back to $S_0$ by intersystem crossing (ISC) to a paramagnetic triplet state ($T_1$) and by inter and intramolecular chemical reactions. As is known in the art, internal conversion is the radiationless transition between energy states of the same spin state. Intersystem crossing (ISC) is a radiationless transition between different spin states. When the riboflavin relaxes from the singlet state to the ground state, it is called fluorescence. When the molecule relaxes from the triplet state ($S_1$) to the ground (unexcited) state ($S_0$) this is called phosphorescence.

The left arrow (first vertical, upward-pointing arrow) in the diagram of FIG. 1 indicates that upon absorption of light energy the riboflavin molecule can go from its ground state ($S_0$) to its excited sate ($S_1$) and become involved in chemical reactions including losing its ribityl moiety to become lumichrome (7,8-dimethylalloxazine). Lumichrome is not photoactive under visible light.

Alternatively, as shown by the second vertical, downward pointing arrow the excited molecule may release its absorbed energy and fluoresce to return to the ground state. The wavy arrows indicate that energy is released.

The excited riboflavin molecule may also relax to its triplet state ($T_1$) through intersystem crossing (ISC) by changing the spin of an electron (spin conversion). The wavy line labeled ISC indicates intersystem crossing. If no oxygen is present, the molecule in its triplet state can phosphoresce (second wavy, downward pointing arrow) and return to its ground state. Or, as indicated by the right arrow, the molecule in its triplet state can react with other molecules in close proximity and return to its ground state. If oxygen is present, the molecule in its triplet state can react with oxygen and return to its ground state producing $^1O_2$ (singlet oxygen). Singlet oxygen can cause DNA strand breaks, further contributing to pathogen kill.

One disadvantage of using the described photochemical methods for pathogen reduction of blood products is that the singlet oxygen species generated in the process of photolysis of riboflavin may cause damage to blood products and compromise their suitability for transfusions. If certain plasma proteins or other components of plasma are present during the photolytic process, the presence of such components may magnify this oxidative process.

One component found in blood plasma and in some commonly used blood storage solutions which, if present, has been suggested to have an effect on the oxidative process of riboflavin, is the nucleoside adenine. Uehara et al. has shown that upon photoactivation, a specific complex is formed between riboflavin and adenine which increases the photodynamic efficiency of riboflavin. The authors showed an accelerative effect of the riboflavin-adenine complex on the photodynamic inactivation of yeast alcohol dehydrogenase. (Kinachino Uehara, Tadashi Mizoguchi, Morio Yonezawa, Saburo Hosomi and Ryogi Hayashi, Effect of Adenine on the Riboflavin-sensitized Photoreaction 1. Effect of Adenine on the Photodynamic Inactivation of Yeast Alcohol Dehydrogenase in the Presence of Ribflavin, J. Vitaminology 17, 148-154 (1971.))

While the formation of a riboflavin-adenine complex may appear to be a desirable side effect in that the presence of the complex would help to decrease the time necessary to pathogen reduce any pathogens contained in and/or around blood or blood components, in fact, the presence of the complex speeds up the oxidative chemistry of riboflavin. The increase in production of reactive oxygen species produced during the oxidation of riboflavin, increases the possibility of cell membrane damage. Cells which are damaged during a pathogen reduction procedure are unable to be reinfused into a patient.

Because adenine is naturally occurring in plasma, in one embodiment of the present invention, the adenine content of fluid to be pathogen reduced is reduced by reducing the plasma content. One method suitable for the plasma reduction step is to dilute the fluid containing plasma with an adenine-free diluting solution. This will reduce the level of adenine in the fluid to be pathogen reduced, thus reducing the amount of adenine available to form a complex with riboflavin. The diluting solution used to reduce the level of adenine to an amount which will not form a complex with riboflavin may be one of many different solutions, including saline; a physiologic buffer, which may comprise a variety of different substances; a solution containing glucose, phosphate or both, which may or may not act as a buffer; a solution containing nutrients; a cryopreservative; an anticoagulant; a cell storage solution known to the art or developed to provide cells with suitable additives to enable them to be stored or infused; or other suitable solution.

The diluting solution should not substantially interfere with the inactivation of microorganisms or substantially destroy the biological activity of the fluid. By "substantially interfere" is meant interference which is sufficient to prevent pathogen reduction from occurring at a desired level.

The diluting solution may also contain a substrate which selectively binds to adenine, effectively removing it from the fluid by rendering it unable to bind to riboflavin. Although in this method adenine may still be present in the fluid to be pathogen reduced, the adenine which is present is not available to bind to riboflavin because it is bound to the adenine-binding substrate. One such adenine-binding substrate which might be used in this invention may be an antibody directed against adenine. The antibody could be added directly to the adenine-containing solution to be pathogen reduced, or could be coupled to a substrate such as polymeric beads. Another substrate which may be used to remove adenine from the fluid may be an ion exchange resin. Such a resin would preferentially bind to adenine based upon the ionic charge of adenine, thus effectively removing adenine from the fluid.

Another method which may be used for reducing the concentration of selected components of plasma such as adenine in a fluid to be pathogen reduced may be by selective filtration. Such methods of filtering out unwanted substances such as adenine from fluids are known in the art. One example of a filter which may be used to selectively remove adenine is a hollow fiber filter. The pore sizes of this filter would be small enough to allow adenine to pass through the pores and be removed from the fluid, leaving the blood component to be pathogen reduced behind.

Another method of selectively filtering out adenine which may be useful with the present invention is to use a filter having an absorption ligand on its surface which selectively binds to adenine, thus effectively removing adenine from the fluid to be pathogen reduced. This method would allows the plasma (minus adenine) to be retained as part of the fluid to be pathogen reduced.

Figure 2:
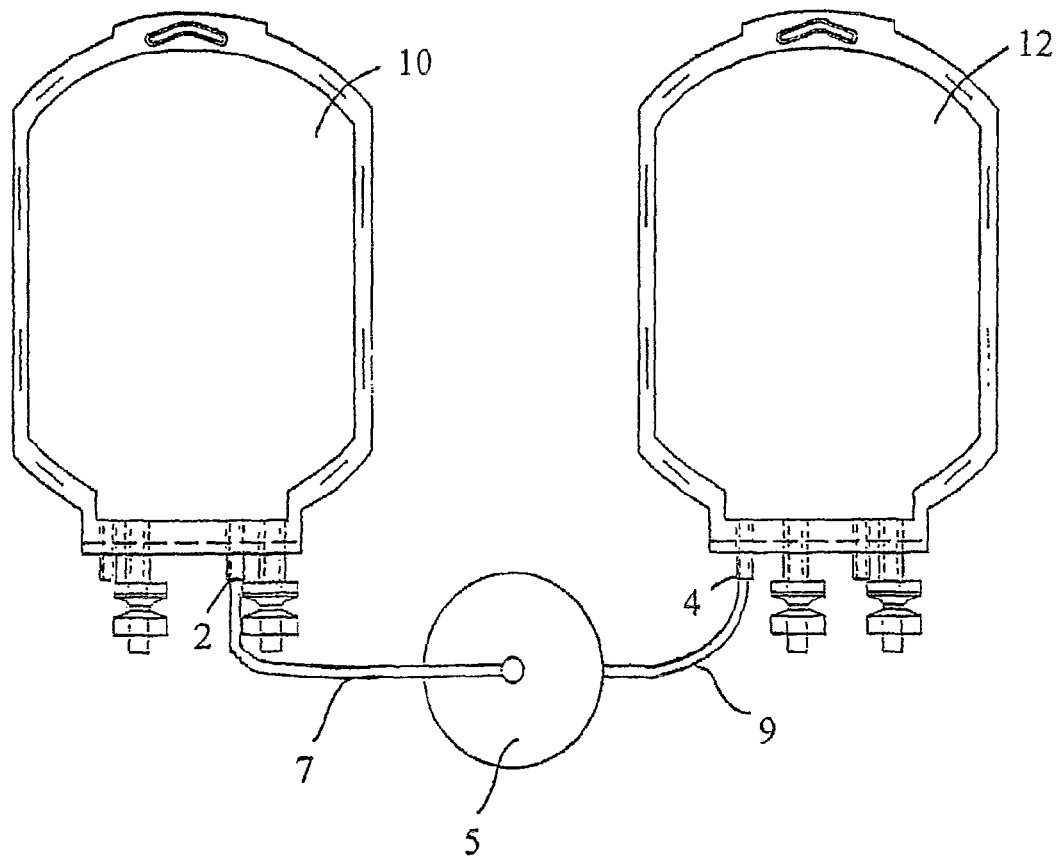
FIG. 2 is a top plan view of a bag set containing a filter for removal of adenine for use in a pathogen reduction procedure.

FIG. 2 depicts one example of a bag set for use in a pathogen reduction procedure containing a filter which may be used to remove adenine from the fluid to be pathogen reduced. Fluid containing blood and plasma, or a collected blood component which has been previously collected in a collection/storage solution containing adenine is contained in bag 10. To substantially remove all adenine which may be contained therein, the fluid to be pathogen reduced flows out of bag 10 via exit port 2 through tubing 7 and into filter 5. Filter 5 may contain filter media having a substrate thereon which selectively binds to adenine, thus removing it from the fluid. After flowing through the filter, the now substantially adenine-free fluid flows through tubing 9 and into bag 12 via port 4. Bag 12 may be prepackaged to contain riboflavin, or riboflavin may be added after the now adenine-free fluid to be pathogen reduced is flowed into bag 12.

In another embodiment, the adenine removal filter may also be contained within one of the bags 10 or 12. The adenine contained in the fluid would bind directly to the filter contained within the bag, and transfer of the now adenine-free fluid into another bag would not be needed.

The adenine reducing step may also be carried out using mechanical means such as centrifugation, to separate the fluid containing adenine from the blood component to be pathogen reduced. This centrifugation step may be done using an apheresis machine such as the COBE Spectra™ or TRIMA® apheresis systems available from Gambro BCT Inc. (Lakewood, Colo., USA) as well as apheresis systems of other manufacturers. The separated blood components may then be resuspended in a suitable solution which does not contain adenine The reduction step may also comprise washing the separated blood component to be pathogen reduced one or more times, as is known in the art. One machine suitable for washing the blood or separated blood components is the COBE 2991 (also available from Gambro BCT Inc.) Washing is generally the addition to the blood component to be pathogen reduced a solution which does not contain adenine to dilute the percentage of plasma (or of collection/storage solution) and consequently the amount of adenine The wash solution is removed and a pathogen reduction solution may be added to resuspend the washed components. The process may be carried out one or more times depending on the initial level of adenine contained in the fluid.

The fluid to be pathogen inactivated may also be initially collected into a solution which does not contain adenine. If this is the case, no step of removing adenine is needed.

In a batch-wise process, after substantially removing any adenine initially present in the plasma or in the collection/storage solution, the fluid to be pathogen reduced is placed into bags which are photopermeable or at least sufficiently photopermeable to allow sufficient radiation to reach their contents to activate the photosensitizer. Photosensitizer is added to each bag to substantially inactivate any pathogens which may be contained therein, and the bag is preferably agitated while irradiating, for a period of time to ensure exposure of substantially all the fluid to radiation.

Figure 3:
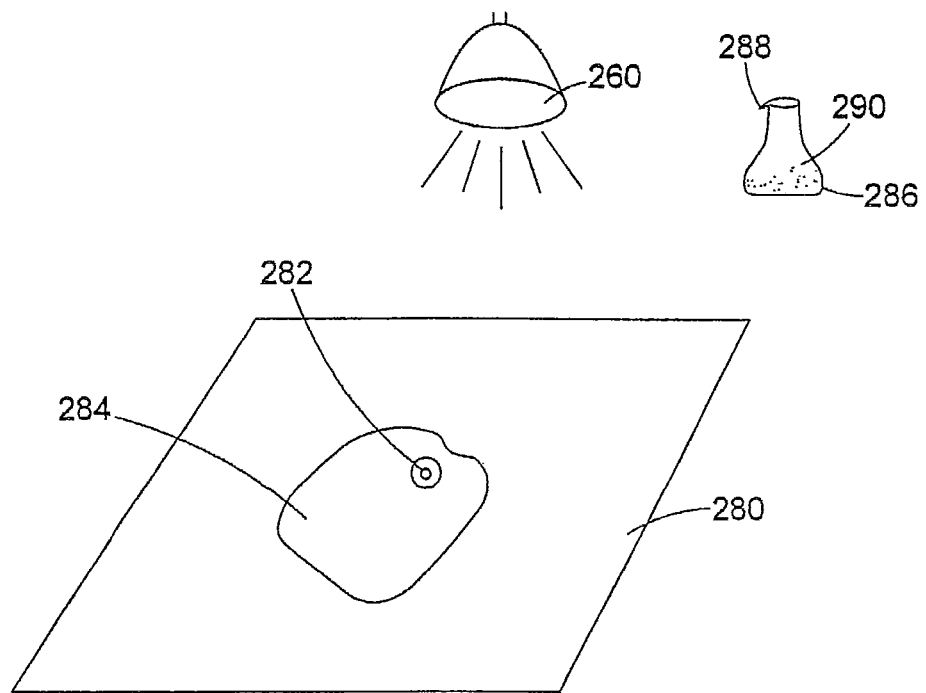
FIG. 3 shows an embodiment of this invention using a bag to contain the fluid being treated with the photosensitizer and a shaker table to agitate the fluid while exposing to photoradiation from a light source.

FIG. 3 depicts an embodiment of this invention in which fluid to be decontaminated and which is substantially adenine-free is placed in a bag 284 equipped with an inlet port 282, through which photosensitizer 290 may be added from flask 286 via pour spout 288. Shaker table 280 is activated to agitate the bag 284 to mix the fluid to be decontaminated and the photosensitizer together while photoradiation source 260 is activated to irradiate the fluid and photosensitizer in bag 284. Alternatively, the bag can be prepackaged to contain photosensitizer and the fluid to be pathogen reduced is thereafter added to the bag.

It is also contemplated that the pathogen reduction process can be done in a flow-through system. In a flow-through process, after substantially removing any adenine initially present in the plasma or in the collection/storage solution, a photosensitizer is added to the fluid containing a blood component which is to be pathogen reduced. The photosensitizer and blood component is flowed past a photoradiation source, and the flow of the material generally provides sufficient turbulence to distribute the photosensitizer throughout the fluid. A mixing step may optionally be added.

EXAMPLES

Blood to be pathogen reduced may be separated into components by any means known in the art.

Example 1

The method of this example requires the removal of substantially all adenine which may be contained in a solution used to resuspend and/or collect platelets to be pathogen reduced. Removal of adenine may be done using any of the methods set forth above. If an adenine-free solution is used to resuspend or collect the platelets to be pathogen reduced, no adenine removal step is needed. After removal of any adenine which may be present, the photosensitizer is mixed with the fluid containing platelets. Mixing may be done by simply adding the photosensitizer or a solution containing the photosensitizer to the platelets to be pathogen reduced. In one embodiment, the material to be decontaminated to which a photosensitizer has been added is flowed past a photoradiation source, and the flow of the material generally provides sufficient turbulence to distribute the photosensitizer throughout the fluid to be pathogen reduced. A mixing step may optionally be added. In another embodiment, the fluid and photosensitizer are placed in a photopermeable container and irradiated in batch mode (see FIG. 2), preferably while agitating the container to fully distribute the photosensitizer and expose all the fluid to the radiation.

The amount of photosensitizer to be mixed with the fluid to be pathogen reduced will be an amount sufficient to adequately inactivate the reproductive ability of a pathogen. Preferably the photosensitizer is used in a concentration of at least about 1 μM up to the solubility of the photosensitizer in the fluid. For 7,8-dimethyl-10-ribityl isoalloxazine a concentration range between about 1 μM and about 160 μM is preferred, preferably about 50 μM.

The wavelength used will depend on the photosensitizer selected, and the type of blood component to be pathogen reduced. For platelets and plasma, a light source is used which provides light in the range of about 200 nm to about 320 nm, and more preferably about 308 nm may be used. For red blood cells, light in the range of about 200 nm to about 600 nm is used, preferably about 447 nm.

The following storage solutions shown in Table 1a and 1b are examples of commonly used platelet storage solutions which may be used with this invention. These solutions may be used to resuspend platelets to be pathogen reduced before the addition of the photo sensitizer, or may be used to resuspend platelets after a pathogen reduction procedure. Other solutions not specifically listed that do not contain adenine may also be used. It should be noted that platelets may also be resuspended in buffer and/or saline as long as no adenine is present.

TABLE 1a

|  | Molecular Weight | PAS II Conc. (mMol/L) | PAS II g/300 mLs | PSM1-pH Conc. (mMol/L) | PSM1-pH g 300 mLs | PlasmaLyte A Conc. (mMol/L) | PlasmaLyte A g/300 mLs |
| --- | --- | --- | --- | --- | --- | --- | --- |
| Sodium Chloride | 58.44 | 115.5 | 2.02 | 98 | 1.72 | 90 | 1.58 |
| Potassium Chloride | 74.55 |  | 0.00 | 5 | 0.11 | 5 | 0.11 |
| Calcium Chloride | 111 |  | 0.00 |  | 0.00 |  | 0.00 |
| Magnesium Chloride | 95.21 |  | 0.00 |  | 0.00 | 3 | 0.09 |
| Magnesium Sulfate | 120.4 |  | 0.00 |  | 0.00 |  | 0.00 |
| Tri-Sodium Citrate | 294.1 | 10 | 0.88 | 23 | 2.03 | 23 | 2.03 |
| Citric Acid | 192.1 |  | 0.00 |  | 0.00 |  | 0.00 |
| Sodium Bicarbonate | 84.01 |  | 0.00 |  | 0.00 |  | 0.00 |
| Sodium Phosphate | 142 |  | 0.00 | 25 | 1.07 |  | 0.00 |
| Sodium Acetate | 82.03 | 30 | 0.74 |  | 0.00 | 27 | 0.66 |
| Sodium Gluconate | 218.1 |  | 0.00 |  | 0.00 | 23 | 1.50 |
| Glucose | 180.2 |  | 0.00 |  | 0.00 |  | 0.00 |
| Maltose | 360.3 |  | 0.00 |  | 0.00 |  | 0.00 |
| Adenine | 135.1 |  | 0.00 |  | 0.00 |  | 0.00 |

Note:
Assumes that all salts are anhydrous

TABLE 1b

|  | Molecular Weight | SetoSol Conc. (mMol/L) | SetoSol g/300 mLs | PAS III Conc. (mMol/L) | PAS III g/300 mLs | PAS Conc. (mMol/L) | PAS g/300 mLs |
| --- | --- | --- | --- | --- | --- | --- | --- |
| Sodium Chloride | 58.44 | 90 | 1.58 | 77 | 1.35 | 110 | 1.93 |
| Potassium Chloride | 74.55 | 5 | 0.11 |  | 0.00 | 5.1 | 0.11 |
| Calcium Chloride | 111 |  | 0.00 |  | 0.00 | 1.7 | 0.06 |
| Magnesium Chloride | 95.21 | 3 | 0.09 |  | 0.00 |  | 0.00 |
| Magnesium Sulfate | 120.4 |  | 0.00 |  | 0.00 | 0.8 | 0.03 |
| Tri-Sodium Citrate | 294.1 | 17 | 1.50 | 12.3 | 1.09 | 15.2 | 1.34 |
| Citric Acid | 192.1 |  | 0.00 |  | 0.00 | 2.7 | 0.16 |
| Sodium Bicarbonate | 84.01 |  | 0.00 |  | 0.00 | 35 | 0.88 |
| Sodium Phosphate | 142 | 25 | 1.07 | 28 | 1.19 | 2.1 | 0.09 |
| Sodium Acetate | 82.03 | 23 | 0.57 | 42 | 1.03 |  | 0.00 |
| Sodium Gluconate | 218.1 |  | 0.00 |  | 0.00 |  | 0.00 |
| Glucose | 180.2 | 23.5 | 1.27 |  | 0.00 | 38.5 | 2.08 |

TABLE 1b-continued

|  | Molecular Weight | SetoSol Conc. (mMol/L) | g/300 mLs | PAS III Conc. (mMol/L) | g/300 mLs | PAS Conc. (mMol/L) | g/300 mLs |
|---|---|---|---|---|---|---|---|
| Maltose | 360.3 | 28.8 | 3.11 |  | 0.00 |  | 0.00 |
| Adenine | 135.1 |  | 0.00 |  | 0.00 |  | 0.00 |

Note:
Assumes that all salts are anhydrous

Example 2

Example 2 is directed toward the removal of adenine in a fluid containing red blood cells to be pathogen reduced. If a riboflavin-adenine complex forms in a solution containing red blood cells, the increased oxidation reactions caused by the presence of the complex may damage the red blood cell membranes, causing hemolysis and increased methemoglobin formation. Methemoglobin formation is undesirable because methemoglobin does not allow the red blood cells to efficiently bind and deliver oxygen.

Figure 4:
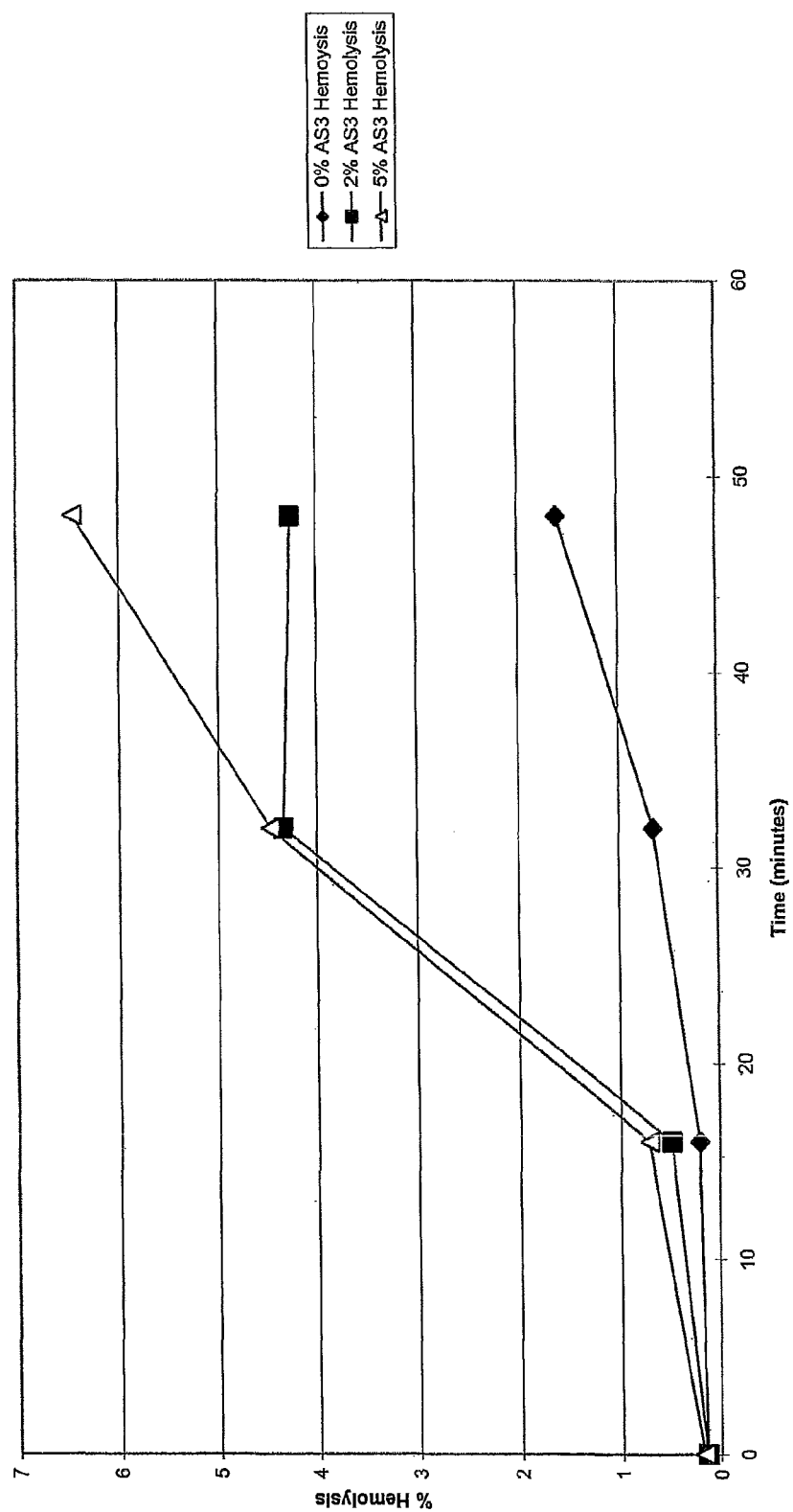
FIG. 4 is a graph comparing the % hemolysis of pathogen reduced red blood cells stored over time in pathogen reduction/storage solutions with and without adenine.

This phenomenon is shown in FIG. 4, which shows the % hemolysis of red blood cells over time in solutions with and without adenine. Red blood cells were suspended in AS3 during a pathogen reduction procedure using riboflavin and visible light. AS3 is an AABB approved red blood cell preservative. AS3 contains sodium chloride, dextrose, adenine, sodium phosphate, sodium citrate and citric acid. As can be seen in FIG. 4, red blood cells suspended in 5% AS3 show the highest percentage of red blood cell hemolysis. Red blood cells subjected to a pathogen reduction procedure in a solution containing no adenine (0% AS3) show less than 2% hemolysis of red blood cells.

Red blood cells to be pathogen reduced should be collected in an anticoagulant-preservation solution which does not contain adenine. Other anticoagulant-preservation solutions not specifically listed in Table 2a and 2b below that do not contain adenine may also be used. As can be seen from Table 2a and 2b, none of the anticoagulant-preservative solutions listed below contain additional adenine TABLE 2a

ANTICOAGULANT PRESERVATIVE SOLUTIONS

|  |  | CPD |  |  | CP2D |  |  |
|---|---|---|---|---|---|---|---|
|  | Molecular Weight | Conc. (mMol/L) | mg/63 ml | mg/100 ml | Conc. (mMol/L) | mg/63 ml | mg/100 ml |
| Sodium Citrate | 294.1 | 89.59 | 1660.00 | 2634.92 | 89.59 | 1660.00 | 2634.92 |
| Citric Acid | 192.1 | 15.53 | 188.00 | 298.41 | 15.53 | 188.00 | 298.41 |
| Dextrose | 180.2 | 141.82 | 1610.00 | 2555.56 | 283.64 | 3220.00 | 5111.11 |
| Monobasic Sodium phosphate | 120 | 18.52 | 140.00 | 222.22 | 18.52 | 140.00 | 222.22 |
| Adenine | 135.1 | 0.00 | 0.00 | 0/00 | 0.00 | 0.00 | 0.00 |

TABLE 2b

ANTICOAGULANT PRESERVATIVE SOLUTIONS

|  |  | ACD-A |  | ACD-B |  |
|---|---|---|---|---|---|
|  | Molecular Weight | Conc. (mMol/L) | mg/100 ml | Conc. (mMol/L) | mg/100 ml |
| Dextrose | 180.2 | 135.96 | 2450.00 | 81.58 | 1470.00 |
| Adenine | 135.1 | 0.00 | 0.00 | 0.00 | 0.00 |

TABLE 2b-continued

ANTICOAGULANT PRESERVATIVE SOLUTIONS

|  |  | ACD-A |  | ACD-B |  |
|---|---|---|---|---|---|
|  | Molecular Weight | Conc. (mMol/L) | mg/100 ml | Conc. (mMol/L) | mg/100 ml |
| Monobasic sodium phosphate | 120 | 0.00 | 0.00 | 0.00 | 0.00 |
| Mannitol | 182.2 | 0.00 | 0.00 | 0.00 | 0.00 |
| Sodium Chloride | 58.45 | 0.00 | 0.00 | 0.00 | 0.00 |
| Sodium Citrate | 294.1 | 74.80 | 2200.00 | 44.88 | 1320.00 |
| Citric Acid | 192.1 | 41.64 | 800.00 | 24.99 | 480.00 |

Alternatively, if previously collected red blood cells are to be pathogen reduced, the cells may be washed before undergoing a pathogen reduction procedure to remove any adenine contained in the solution used to collect and store the previously collected cells. The washing procedure may be used to remove plasma (which contains endogenous adenine), or to remove adenine from blood products which were previously collected and stored in synthetic storage solutions or anticoagulants containing exogenous adenine One red blood cell wash process which may be used with the present invention is described below. However, any process for washing cells known in the art may be used. Red cells can be washed by manual centrifugation or with an automated cell washer such as the COBE 2991 (available from Gambro BCT, Lakewood, Colo., USA). The 2991 washes the red cells with 700 mL of 0.9% sodium chloride and 300 mL of 500 μM riboflavin in 0.9% sodium chloride.

The product of the wash step is a suspension of concentrated red blood cells at a 60 to 70% hematocrit. The washed red cells are mixed with a solution containing 550 μM riboflavin in a 0.9% sodium chloride to obtain a suspension with a hematocrit of 50% and a volume of 276 mL. The solution may also be any of the anticoagulant-preservative solutions set forth in the tables above.

The washed red cells are transferred from the cell-washing bag to a bag suitable for illumination and subsequent dilution to a 50% hematocrit. The washed red cells and riboflavin are typically illuminated with visible light at a wavelength of 447 nm and 120 J/cm2. After illumination, the extracellular fluid is expressed off and a storage solution which may or may not contain adenine is added in an amount necessary to increase the hematocrit of the red cells to 55%. The pathogen reduced red blood cells may then be stored or directly reinfused into a patient.

Removal of adenine may also be done using any of the other methods set forth above.

The addition of "quenchers" or oxygen scavengers, may be used to enhance the pathogen reduction process by further reducing the extent of non-specific cell-damaging chemistry. Examples of quenchers which may be used in this invention include electron rich amino acids such as histidine, methionine, tyrosine and tryptophan. Nucleotides such as cysteine, guanosine and adenoside monophosphate. Sulfhidryl quenchers such as N-acetyl-L-cysteine and glutathione. Antioxdants such as trolox, Vitamin E and alpha-tocopherol acetate. Other quenchers such as propyl gallate, ascorbate, mercaptopropionylglycine, dithiothreotol, nicotinamide, BHT, BHA, lysine, serine, glucose, mannitol, glycerol, and mixtures thereof may also be used. Quenchers may be added to the fluid to be pathogen reduced either before or after the removal of adenine It will be appreciated that the instant specification and claims are set forth by way of illustration and not of limitation, and that various modifications and changes may be made without departing from the spirit and scope of the present invention.

We claim:

1. A method for treating a quantity of platelets to reduce pathogens which may be present therein, the method comprising:

adding a volume of a washing solution to a fluid comprising: platelets and a platelet storage solution comprising adenine;

washing the fluid to remove adenine and create a washed fluid comprising the platelets;

adding a pathogen reduction-effective, non-toxic amount of 7,8-dimethyl-10-ribityl isoalloxazine photosensitizer to the washed fluid; and reducing pathogens in the washed fluid by exposing the washed fluid containing the photosensitizer and the platelets to photoradiation of sufficient wavelength and energy to activate the photosensitizer.

2. A method for treating a quantity of red blood cells to reduce pathogens which may be present therein, the method comprising:

adding a volume of a washing solution to a fluid comprising: red blood cells and a red blood cell storage solution comprising adenine;

washing the fluid to remove adenine and create a washed fluid comprising the red blood cells;

adding a pathogen reduction-effective, non-toxic amount of 7,8-dimethyl-10-ribityl isoalloxazine photosensitizer to the washed fluid; and reducing pathogens in the washed fluid by exposing the washed fluid containing the photosensitizer and the red blood cells to photoradiation of sufficient wavelength and energy to activate the photosensitizer.

3. The method of claim 2 wherein the washing further comprises a plurality of washing steps.

4. The method of claim 2 wherein the adding the pathogen reduction-effective, non-toxic amount of 7,8-dimethyl-10-ribityl isoalloxazine photosensitizer step, further comprises placing the washed fluid in a container transparent to photoradiation, adding the photosensitizer to the fluid in the container and agitating the container.

* * * * *